United States Patent
Oshio et al.

(10) Patent No.: US 9,801,404 B2
(45) Date of Patent: *Oct. 31, 2017

(54) IGF-1 PRODUCTION-PROMOTING AGENT

(71) Applicant: MORINAGA MILK INDUSTRY CO., LTD., Tokyo (JP)

(72) Inventors: Kazutaka Oshio, Kanagawa (JP); Hirohiko Nakamura, Kanagawa (JP); Yasuyuki Sakata, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 58 days.

This patent is subject to a terminal disclaimer.

(21) Appl. No.: 14/651,423

(22) PCT Filed: Jun. 28, 2013

(86) PCT No.: PCT/JP2013/067866
§ 371 (c)(1),
(2) Date: Jun. 11, 2015

(87) PCT Pub. No.: WO2014/103410
PCT Pub. Date: Jul. 3, 2014

(65) Prior Publication Data
US 2015/0328182 A1   Nov. 19, 2015

(30) Foreign Application Priority Data

Dec. 26, 2012 (JP) ................. 2012-283414

(51) Int. Cl.
| A61K 31/352 | (2006.01) |
| A23L 1/30 | (2006.01) |
| A23L 2/52 | (2006.01) |
| A61K 47/40 | (2006.01) |
| A61K 36/752 | (2006.01) |
| A61K 9/00 | (2006.01) |
| A21D 2/14 | (2006.01) |
| A23L 33/105 | (2016.01) |

(52) U.S. Cl.
CPC .............. *A23L 1/3002* (2013.01); *A21D 2/14* (2013.01); *A23L 2/52* (2013.01); *A23L 33/105* (2016.08); *A61K 9/0095* (2013.01); *A61K 31/352* (2013.01); *A61K 36/752* (2013.01); *A61K 47/40* (2013.01); *A23V 2002/00* (2013.01)

(58) Field of Classification Search
None
See application file for complete search history.

(56) References Cited

U.S. PATENT DOCUMENTS

| 2002/0040052 A1 | 4/2002 | Ito et al. |
| 2007/0088078 A1 | 4/2007 | Dushenkov et al. |
| 2007/0213282 A1 | 9/2007 | Sasaki |
| 2012/0141615 A1 | 6/2012 | Taguchi et al. |
| 2012/0289461 A1 | 11/2012 | Miura |
| 2014/0018292 A1 | 1/2014 | Miura |
| 2014/0356462 A1 | 12/2014 | Sakata et al. |

FOREIGN PATENT DOCUMENTS

| EP | 2799083 A1 | 11/2014 |
| JP | 06-72870 A | 3/1994 |
| JP | 06072870 | * 3/1994 |
| JP | 2000-169374 A | 6/2000 |
| JP | 2001-240539 A | 9/2001 |
| JP | 2001240539 | * 9/2001 |
| JP | 2004-083417 A | 3/2004 |
| JP | 2005-206546 A | 8/2005 |
| JP | 2005-213178 A | 8/2005 |
| JP | 2006-328031 A | 12/2006 |
| JP | 3946238 B1 | 4/2007 |
| JP | 2007-204379 A | 8/2007 |
| JP | 2007-332118 A | 12/2007 |
| JP | 2007-332119 A | 12/2007 |
| JP | 2008-74723 A | 4/2008 |
| JP | 2008074723 | * 4/2008 |
| JP | 2009-196989 A | 9/2009 |
| JP | 2009-263262 A | 11/2009 |
| JP | 2010-150177 A | 7/2010 |
| JP | 2011-037798 A | 2/2011 |
| JP | 2011-157345 A | 8/2011 |
| JP | 2011-241162 A | 12/2011 |
| JP | 2012-121856 A | 6/2012 |
| JP | 2012-180307 A | 9/2012 |
| JP | 2012180307 | * 9/2012 |
| JP | 2012-232916 A | 11/2012 |
| JP | 2012232916 | * 11/2012 |
| WO | WO 2009/035055 A1 | 3/2009 |

OTHER PUBLICATIONS

Evans, Skeletal muscle loss: cachexia, sarcopenia, and inactivity, Am. J. Clin. Nutr. 2010; 91 (suppl): 1123S-7S.*
International Search Report for International Application No. PCT/JP2013/067866, dated Jul. 30, 2013.
Burnett et al., "RAFT1 phosphorylation of the translational regulators p70 S6 kinase and 4E-BP1," *PNAS*, vol. 95, pp. 1432-1437 (Feb. 1998).
Cheng et al., "Tangeretin and its metabolite 4'-hydroxytetramethoxyflavone attenuate EGF-stimulated cell cycle progression hepatocytes; role of inhibition at the level of mTOR/p70S6K," *British Journal of Pharmacology*, vol. 162, pp. 1781-1791 (2011).

(Continued)

*Primary Examiner* — Svetlana M Ivanova
(74) *Attorney, Agent, or Firm* — Knobbe, Martens, Olson & Bear LLP

(57) ABSTRACT

An extract of *Citrus depressa*, preferably a water and/or organic solvent extract of a fruit of leaf of *Citrus depressa*, a supercritical extract of a fruit of leaf of *Citrus depressa*, or a subcritical extract of a fruit of leaf of *Citrus depressa*, which comprise 0.3 mass % or more of a polymethoxyflavonoid more than in terms of solid matter, for example, an extract of *Citrus depressa* comprising 0.2 mass % or more of nobiletin and/or 0.1 mass % or more of tangeretin in terms of solid matter, or a polymethoxyflavonoid such as nobiletin or tangeretin is used as an active ingredient of an IGF-1 production-promoting agent.

7 Claims, No Drawings

(56) References Cited

OTHER PUBLICATIONS

Dufner et al., "Ribosomal S6 Kinase Signaling and the Control of Translation," *Experimental Cell Research*, vol. 253, pp. 100-109 (1999).
Fingar et al., "Target of rapamycin (TOR): an integrator of nutrient and growth factor signals and coordinator of cell growth and cell cycle progression," *Oncogene*, vol. 23, pp. 3151-3171 (2004).
Gingras et al., "Regulation of translation initiation by FRAP/mTOR," *Genes & Development*, vol. 15, pp. 807-826 (2001).
Isotani et al., "Immunopurified Mammalian Target of Rapamycin Phosphorylates and Activates p70 S6 Kinase α in Vitro," *The Journal of Biological Chemistry*, vol. 274(48), pp. 34493-34498 (1999).
Koga et al., "Comparative Study on Nobiletin Metabolism with Liver Microsomes from Rats, Guinea Pigs and Hamsters and Rat Cytochrome P450," *Biological and Pharmaceutical Bulletin*, vol. 30(12), pp. 2317-2323 (2007).
Partlow et al., "Effects of a Nerve-Growth Factor, Embryo Age and Metabolic Inhibitors on Growth of Fibres and on Synthesis of Ribonucleic Acid and Protein in Embryonic Sympathetic Ganglia," *Journal of Neurochemistry*, vol. 18, pp. 2101-2118 (1971).
Office Action issued in Japanese Patent Application No. 2014-554176, dated Jul. 26, 2016.
Extended European Search Report issued in corresponding European Patent Application No. 13866826.4, dated Jul. 15, 2016.

\* cited by examiner

IGF-1 PRODUCTION-PROMOTING AGENT

CROSS-REFERENCE TO RELATED APPLICATIONS

This application is the U.S. National Phase under 35 U.S.C. §371 of International Application PCT/JP2013/067866, filed Jun. 28, 2013, which claims priority to JP Application No. 2012-283414, filed Dec. 26, 2012.

TECHNICAL FIELD

The present invention relates to an IGF-1 production-promoting agent. An IGF-1 production-promoting agent can be used as a drug, and for foods and feeds.

BACKGROUND ART

Protein synthesis is stimulated by changes of physiological conditions such as those provided by ingestion of foods, exercise, and sleep. Growth hormones secreted from the hypophysis upon receiving these stimuli directly or indirectly act on target organs. When growth hormones indirectly act, insulin-like growth factor 1 (IGF-1) secreted from the liver stimulated by a growth hormone is transported by blood throughout the whole body, and acts on a target organ. It is known that most of human cells, especially cells of muscle, bone, liver, kidney, nerve, skin, and lung, are influenced by IGF-1.

For example, if IGF-1 binds to a target organ, or a receptor of each cell of a tissue, signal transfer starts within the cell. There is the mammalian rapamycin target protein (mTOR) downstream from this signal transfer. The signal transfer system via mTOR works as a sensor for the amino acid balance in the cellular environment of mammals, and participates in the protein synthesis through control of activities of two of the important regulatory factors involved in the translation of proteins, the S6 kinase 1 (S6K1, Non-patent document 1) and the initiation factor 4E-binding protein (4E-BP1, Non-patent document 2) (Patent document 1, Non-patent documents 3 and 4). It is also known that S6K1 and 4E-BP1 activated by being phosphorylated (Non-patent document 5).

Therefore, IGF-1 concentration and activated states of S6K1 and 4E-BP1 (phosphorylated states) are frequently used as indexes of protein synthesis.

In patent documents concerning promotion of protein synthesis, there have been reported a whey protein hydrolysate (Patent document 2), fish ovary membrane (Patent document 3), 11β-hydroxy-4-androstene-3,17-dione (Patent document 4), sterol glycoside derived from germinated brown rice (Patent document 5), and so forth.

Although there are known several substances having a protein synthesis-promoting action as described above, it is not known that extract of *Citrus depressa*, or a polymethoxyflavonoid such as nobiletin and tangeretin has a protein synthesis-promoting action.

Further, in patent documents concerning the IGF-1 production-promoting action, there have been reported gentiopicrin (Patent document 6), swertiamarin (Patent document 7), *Angelica keiskei* extract and/or luteolin-7-O-glucoside (Patent document 8), molecular species including Fc region of immunoglobulin G (Patent document 9), sterol glycoside derived from germinated brown rice (Patent document 5), ε-viniferin (Patent document 10), *Paeonia albiflora* extract (Patent document 11), and so forth.

Although there have been reported several substances having the IGF-1 production-promoting action as described above, it is not known that extract of *Citrus depressa*, or a polymethoxyflavonoid such as nobiletin and tangeretin show the IGF-1 production-promoting action.

As a plant-derived health food raw material, extract of *Citrus depressa* attracts attention. Various efficacies of polymethoxyflavonoids such as nobiletin and tangeretin contained in extract of *Citrus depressa* have been found to date. For example, it is reported that nobiletin has such actions as anti-hypertension and anti-cancer actions (Patent document 12), heart disease preventing and treating actions (Patent document 13), and antiulcer action (Patent document 14). Further, it has been reported that polymethoxyflavonoids such as tangeretin and nobiletin have a neovascularization suppressing action (Patent document 15). Furthermore, it is known that flavonoids contained in *Citrus* species such as *Citrus depressa* have a blood pressure elevation suppressing action (Patent document 16).

Furthermore, although there has been reported that nobiletin and tangeretin have a neurite outgrowth action (Patent document 17), it is known that synthesis of new protein is not required for the neurite outgrowth (Non-patent document 6). Further, although possibility of treatment of peripheral nerve functional disorders such as amyotrophic lateral sclerosis with them is also mentioned in Patent document 17, the object of this treatment is limited to improvement of a pathological condition caused by neurite outgrowth, and the patent document suggests neither suppression of muscular atrophy nor synthesis of myoproteins.

As described above, there have been reported various kinds of efficacies of extract of *Citrus depressa*, or polymethoxyflavonoids such as nobiletin and tangeretin, but it is not known that such extract or substances have an IGF-1 production-promoting action or a protein synthesis-promoting action.

Further, there is also known a muscular fiber type shift inhibitor using a polyphenol contained in fruits of Rosaceae plants such as apple trees, for example, procyanidin, as an active ingredient (Patent document 18). However, the fruit-derived polyphenol as the active ingredient of this muscular fiber type shift inhibitor is limited to those derived from fruits of Rosaceae plants, but polyphenols derived from Rosaceae plants contain polymethoxyflavonoids only at a low content.

Such polymethoxyflavonoids as mentioned above are scarcely contained in fruit juice, but are mostly contained in pericarps. Therefore, only by squeezing fruits, these polymethoxyflavonoids are obtained only at a low content.

Polymethoxyflavonoids constitute one class of flavonoid, have a special structure in which a plurality of phenolic hydroxyl groups are methylated, and are mainly contained in *Citrus* species. It has also been reported that polymethoxyflavonoids such as nobiletin or tangeretin are metabolized in the liver after ingestion. For example, methoxy groups of nobiletin are converted into hydroxyl groups by metabolism in the liver of rat, and nobiletin derivatives having 4'-OH, 7-OH, 6-OH, 3',4'-diOH, 6,7-diOH or the like are generated as metabolites. Further, it has been reported that, from tangeretin, tangeretin derivatives having 4'-OH, 3',4'-diOH, 7,4'-diOH, 6,7-diOH or the like are generated as metabolites (Non-patent document 7).

PRIOR ART REFERENCES

Patent Documents

Patent document 1: Japanese Patent Laid-open (Kokai) No. 2007-204379

Patent document 2: Japanese Patent Laid-open (Kokai) No. 2011-160757
Patent document 3: Japanese Patent No. 3946238
Patent document 4: Japanese Patent Laid-open (Kokai) No. 2000-169374
Patent document 5: Japanese Patent Laid-open (Kokai) No. 2011-157345
Patent document 6: Japanese Patent Laid-open (Kokai) No. 2009-196989
Patent document 7: Japanese Patent Laid-open (Kokai) No. 2009-263262
Patent document 8: Japanese Patent Laid-open (Kokai) No. 2010-150177
Patent document 9: International Patent Publication WO2009/035055
Patent document 10: Japanese Patent Laid-open (Kokai) No. 2011-241162
Patent document 11: Japanese Patent Laid-open (Kokai) No. 2012-121856
Patent document 12: International Patent Publication WO2006/49234
Patent document 13: Japanese Patent Laid-open (Kokai) No. 2011-37798
Patent document 14: Japanese Patent Laid-open (Kokai) No. 6-72870
Patent document 15: Japanese Patent Laid-open (Kokai) No. 2004-83417
Patent document 16: Japanese Patent Laid-open (Kokai) No. 2001-240539
Patent document 17: Japanese Patent Laid-open (Kokai) No. 2002-60340
Patent document 18: Japanese Patent Laid-open (Kokai) No. 2006-328031

Non-Patent Documents

Non-patent document 1: Burnett, P. E. et al., PNAS, 95, 1432-1437 (1998)
Non-patent document 2: Isotani, S. et al., J. Biol. Chem., 274, 34493-34498 (1999)
Non-patent document 3: Gingras, A-C. et al., Genes & Dev., 15, 807-826 (2001)
Non-patent document 4: Fingar, D. C. and Blenis, J. Oncogene, 23, 3151-3171 (2004)
Non-patent document 5: Exp. Cell Res., 253 (1), 100-109 (1999)
Non-patent Document 6: Partlow, L. M. and Larrabee, M. G., J. Neurochem., 18, 2101-2118 (1971)
Non-patent document 7: Koga, N. et al., Biol. Pharm. Bull., 30(12), 2317-2323 (2007)

SUMMARY OF THE INVENTION

Object to be Achieved by the Invention

An object of the present invention is to provide an IGF-1 production-promoting agent that can be taken safely, and a food or drink comprising it.

Means for Achieving the Object

The inventors of the present invention conducted various researches in order to achieve the aforementioned object. As a result, they found that an extract of *Citrus depressa*, or a polymethoxyflavonoid as an ingredient thereof had a superior IGF-1 production-promoting action, and accomplished the present invention.

The present invention thus provides an IGF-1 production-promoting agent comprising a polymethoxyflavonoid as an active ingredient.

According to a preferred embodiment of the IGF-1 production-promoting agent of the present invention, the polymethoxyflavonoid is nobiletin and/or tangeretin.

The present invention also provides an IGF-1 production-promoting agent comprising an extract of *Citrus depressa* comprising 0.3 mass % or more of a polymethoxyflavonoid in terms of solid matter as an active ingredient.

According to a preferred embodiment of the IGF-1 production-promoting agent of the present invention, the IGF-1 production-promoting agent further comprise a clathrating agent that makes the polymethoxyflavonoid water-soluble.

According to a preferred embodiment of the IGF-1 production-promoting agent of the present invention, the clathrating agent is cyclodextrin, and content thereof is 0.1 to 95 mass % based on the total mass of the solid matter of the extract of *Citrus depressa* and cyclodextrin.

According to another preferred embodiment of the IGF-1 production-promoting agent of the present invention, the IGF-1 production-promoting agent comprise an extract of *Citrus depressa* comprising 0.2 mass % or more of nobiletin, and/or 0.1 mass % or more of tangeretin in terms of solid matter as an active ingredient.

According to another preferred embodiment of the IGF-1 production-promoting agent of the present invention, the IGF-1 production-promoting agent is used for promotion of protein synthesis.

The present invention also provides a food or drink comprising the aforementioned IGF-1 production-promoting agent in an amount of 0.3 mass % or more as content of the polymethoxyflavonoid in terms of solid matter.

The present invention further provides a food or drink comprising the IGF-1 production-promoting agent comprising nobiletin in an amount of 0.2 mass % or more as content of nobiletin in terms of solid matter.

The present invention also provides a food or drink comprising the IGF-1 production-promoting agent comprising tangeretin in an amount of 0.1 mass % or more as content of tangeretin in terms of solid matter.

The present invention further provides a food or drink comprising the IGF-1 production-promoting agent comprising nobiletin and tangeretin in such an amount that nobiletin content is 0.2 mass % or more in terms of solid matter, and tangeretin content is 0.1 mass % or more in terms of solid matter.

The present invention also provides use of a polymethoxyflavonoid in manufacture of an IGF-1 production-promoting agent.

According to a preferred embodiment of the aforementioned use of the present invention, the polymethoxyflavonoid is nobiletin and/or tangeretin.

The present invention further provides use of an extract of *Citrus depressa* comprising a polymethoxyflavonoid in an amount of 0.3 mass % or more in terms of solid matter in manufacture of an IGF-1 production-promoting agent.

According to a preferred embodiment of the aforementioned use of the present invention, the extract of *Citrus depressa* is used together with a clathrating agent that makes the polymethoxyflavonoid water-soluble.

According to another preferred embodiment of the aforementioned use of the present invention, the clathrating agent is cyclodextrin, and content thereof is 0.1 to 95 mass % based on the total mass of the solid matter of the extract of *Citrus depressa* and cyclodextrin.

The present invention further provides use of an extract of *Citrus depressa* comprising 0.2 mass % or more of nobiletin, and/or 0.1 mass % or more of tangeretin in terms of solid matter in manufacture of an IGF-1 production-promoting agent.

According to a preferred embodiment of the aforementioned use of the present invention, the IGF-1 production-promoting agent is used for promotion of protein synthesis.

MODES FOR CARRYING OUT THE INVENTION

Hereafter, preferred embodiments of the present invention will be explained in detail. However, the present invention is not limited to the following preferred embodiments, but can be freely modified within the scope of the present invention.

The IGF-1 production-promoting agent of the present invention comprises a polymethoxyflavonoid as an active ingredient. In another embodiment of the IGF-1 production-promoting agent of the present invention, the IGF-1 production-promoting agent comprises an extract of *Citrus depressa*, especially an extract of *Citrus depressa* comprising 0.3 mass % or more of a polymethoxyflavonoid in terms of solid matter, as an active ingredient.

Polymethoxyflavonoids comprised in *Citrus depressa* or an extract thereof mainly have a structure represented by the following formula, and specific examples include nobiletin, tangeretin, 5-demetylated nobiletin, 8-demethoxylated nobiletin (sinensetin), 6-demethoxylated tangeretin, 6-demethoxylated nobiletin, citromitin, 5,6,7,8,4-pentamethoxyflavanone, and so forth. Among these, nobiletin and tangeretin are preferred.

In the following chemical formula, R, $R_1$, $R_2$, $R_3$, and $R_4$ are OMe, OMe, H, Me, and OMe, respectively, in nobiletin, or OMe, H, H, Me, and OMe, respectively, in tangeretin (Me represents methyl group, OMe represents methoxy group, and H represents hydrogen).

The polymethoxyflavonoid may consist of a single kind of polymethoxyflavonoid or a mixture of arbitrary two or more kinds of polymethoxyflavonoids.

[Formula 1]

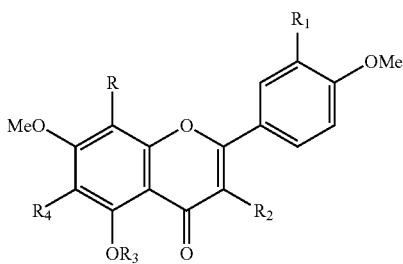

(In the formula, R, $R_1$, $R_2$, and $R_4$ independently represent hydrogen atom or methoxy group, and $R_3$ represents hydrogen atom or methyl group.)

The polymethoxyflavonoid may be extracted from a fruit, leaf, root, stem etc. of a *Citrus* species or another plant comprising that substance, or may be produced by chemical synthesis.

The extract of *Citrus depressa* can be produced by, for example, extraction of fruit and/or leaf of *Citrus depressa* with water and/or an organic solvent. The organic solvent may comprise water. *Citrus depressa* (Shiikuwasha) is a kind of *Citrus* species belonging to the family Rutaceae.

The fruit and/or leaf may be the whole fruit and/or leaf, or may be a part thereof. For example, the fruit may be pulp or pericarp. Further, the fruit and/or leaf may be used as they are, or may be used after crushing, for example, as a finely crushed product of the fruit and/or leaf having a size of nanometer order. Further, the fruit and/or leaf may be a juice extraction residue of a fruit and/or leaf, or a part thereof. Hereafter, these fruit and/or leaf, a part thereof, crushed product thereof, and juice extraction residue thereof may be referred to as "*Citrus depressa* fruit and/or leaf etc."

Examples of the organic solvent include alcohols such as methanol, ethanol, propanol, isopropanol, and butanol, esters such as ethyl acetate, acetone, hexane, chloroform, diethyl ether, acetonitrile, these organic solvents comprising water, combination of any of these organic solvents and organic solvents comprising water, and so forth, but among these, ethanol is preferred. Although water content in the organic solvent is not particularly limited, it is preferably 0 to 90 mass %, and more preferably 0 to 40 mass %.

Although amount of the organic solvent with respect to the *Citrus depressa* fruit and/or leaf etc. used in the extraction with the organic solvent is not particularly limited, ratio (weight ratio) of the *Citrus depressa* fruit and/or leaf etc.: organic solvent is preferably 1:0.5 to 1:100, and more preferably 1:1 to 1:20.

Although the method of the extraction is not particularly limited, examples include, for example, a method of adding an organic solvent to *Citrus depressa* fruit and/or leaf etc., performing extraction preferably for 5 minutes to 3 hours with stirring, and then collecting the liquid layer by a solid/liquid separation means such as filtration or centrifugal separation.

Further, after the extraction or before drying process, it is preferable to add a clathrating agent for making the polymethoxyflavonoid water-soluble. If such a clathrating agent is used, effects of improving water solubility, digestion and absorption, and flavor of the polymethoxyflavonoid can be expected. As the clathrating agent, it is preferable to use a compound for clathrate such as cyclodextrin. In the case of cyclodextrin, amount of the clathrating agent is preferably 0.1 to 95 mass %, and more preferably 1 to 90 mass %, based on the total mass of the solid matter of the extract of *Citrus depressa* and cyclodextrin.

The extract of *Citrus depressa* of the present invention can also be produced by supercritical extraction. Specifically, it can be produced by, for example, subjecting frozen and crushed *Citrus depressa* fruit or leaf, or *Citrus depressa* fruit or leaf powdered by lyophilization or hot air-drying to supercritical extraction performed under the following conditions (a) to (d).

(a) Extraction solvent is carbon dioxide (carbon dioxide gas).
(b) Extraction temperature is 31.1 to 120° C., preferably 40 to 100° C., and particularly preferably 60 to 80° C.
(c) Pressure is 7.38 to 60 MPa, preferably 20 to 40 MPa, and particularly preferably 25 to 35 MPa.
(d) Extraction time is 5 to 70 minutes, preferably 10 to 50 minutes, and particularly preferably 20 to 30 minutes.

As the extraction fluid, it is possible to use supercritical propane, supercritical ethylene, supercritical 1,1,1,2-tetrafluoroethane, or the like, in order to improve extraction efficiency of the *Citrus depressa* fruit and/or leaf etc. However, in order to increase safety as food or drink, it is preferable to use carbon dioxide (carbon dioxide gas). The extraction temperature may be appropriately chosen to be in the temperature range of 31.1 to 120° C., but in order to improve the extraction efficiency and increase the content of the polymethoxyflavonoid, especially nobiletin and/or tangeretin, it is preferably in the range of 40 to 100° C., and more preferably in the range of 60 to 80° C. The pressure is preferably in the range of 7.38 to 60 MPa, and more preferably in the range of 20 to 40 MPa. Further, in the present invention, ethanol, water, or the like may be used as an entrainer, in order to improve the extraction efficiency.

Although the extraction time may be appropriately chosen according to the temperature or pressure, it is, for example, preferably in the range of 10 to 50 minutes, and more preferably 20 to 30 minutes.

The extraction operation can be performed by using a commercially available apparatus.

The extract of *Citrus depressa* of the present invention can also be produced by subcritical extraction. Specifically, it can be produced by, for example, subjecting frozen and crushed *Citrus depressa* fruit or leaf, or *Citrus depressa* fruit or leaf powdered by lyophilization or hot air-drying to subcritical extraction performed under the following conditions (a) to (d).
(a) Extraction solvent is water.
(b) Extraction temperature is 140 to 374° C., and preferably 140 to 180° C.
(c) Pressure is 3 to 22 MPa, and preferably 3 to 10 MPa.
(d) Extraction time is 0 to 10 minutes, and preferably 0 to 5 minutes.

The extraction time of 0 minute means that immediately after the temperature is raised to the objective extraction temperature from the start of the extraction, the temperature is lowered by cooling to the level at the start of the extraction.

Examples of the extraction fluid used for the subcritical extraction include, for example, water and carbon dioxide. However, in order to increase safety as food or drink, it is preferable to use water.

In the case of using water as the extraction fluid, the extraction temperature may be appropriately chosen to be in the temperature range of 140 to 374° C., but in order to improve the extraction efficiency and increase the content of the polymethoxyflavonoid, especially nobiletin and/or tangeretin, it is preferably in the range of 140 to 180° C. The pressure is preferably in the range of 3 to 10 MPa in the case of using water as the extraction fluid.

Although the extraction time may be appropriately chosen according to the temperature or pressure, it is preferably in the range of 0 to 10 minutes, and more preferably 0 to 5 minutes.

The extraction operation can be performed by using a commercially available apparatus.

Yields of nobiletin and tangeretin in an extract obtained as described above by the extraction method using water, an organic solvent, or an organic solvent comprising water, supercritical extraction, or subcritical extraction are usually about 0.001 to 3 mass %, and about 0.0001 to 2 mass %, respectively, based on the weight of *Citrus depressa* fruit and/or leaf etc.

The extract of *Citrus depressa* obtained as described above comprises 0.1 mass % or more, preferably 0.3 mass % or more, more preferably 0.6 mass % or more, still more preferably 1 mass % or more, further preferably 3 mass % or more, and particularly preferably 10 mass % or more, of the polymethoxyflavonoid in terms of solid matter. Further, such an extract of *Citrus depressa* comprises 0.07 mass % or more, preferably 0.2 mass % or more, more preferably 0.4 mass % or more, still more preferably 0.7 mass % or more, further preferably 2 mass % or more, and particularly preferably 6 mass % or more, of nobiletin in terms of solid matter, and/or 0.04 mass % or more, preferably 0.1 mass % or more, more preferably 0.2 mass % or more, still more preferably 0.4 mass % or more, further preferably 1 mass % or more, and particularly preferably 3 mass % or more, of tangeretin in terms of solid matter.

The phrase "in terms of solid matter" has the same meaning as "as amount of solid matter (solid content)". Further, expression that the agent, food or the like comprises X % or more of the extract of *Citrus depressa*, polymethoxyflavonoid, nobiletin, or tangeretin "in terms of solid matter" means that the ratio of the amount of the solid matter of the extract of *Citrus depressa*, polymethoxyflavonoid, nobiletin, or tangeretin to the amount of the solid matter of the agent, food or the like is X %.

The extract may be used as it is, or may be used after concentration, and the solvent may be partially or completely removed. The concentration or removal of the solvent can be carried out by such methods as various chromatography techniques, distillation, solidification by drying, and recrystallization. It is preferable to remove, in particular, organic solvents desirably not to be comprised in a drug or food or drink, such as methanol, propanol, butanol, ethyl acetate, acetone, hexane, chloroform, and diethyl ether. Further, in order to increase the content of the polymethoxyflavonoid, especially nobiletin and/or tangeretin, the extract may be fractionated. The content of the polymethoxyflavonoid such as nobiletin and/or tangeretin can be measured by HPLC or the like.

Such an extract of *Citrus depressa* or polymethoxyflavonoid as described above can be used as it is as an active ingredient of the IGF-1 production-promoting agent (henceforth also referred to as "agent of the present invention"), food, drink, or feed. The extract of *Citrus depressa* or polymethoxyflavonoid may be in the form of a solution, or it may also be lyophilized or spray-dried in a conventional manner, then stored and used as powder.

The agent of the present invention can be used as a drug or an active ingredient thereof as one embodiment. As the agent of the present invention, an extract of *Citrus depressa* as it is, or the polymethoxyflavonoid, or nobiletin and/or tangeretin, or a combination of these with a pharmaceutically acceptable carrier can be orally administered to a mammal including human.

Preparation form of the agent of the present invention is not particularly limited, and examples include tablets (including sugar-coated tablets, enteric coated tablets, and buccal tablets), powders, capsules (including enteric capsules and soft capsules), granules (including coated granules), pills, troches, enclosed liposome agents, solutions, pharmaceutically acceptable sustained release preparations of these, and so forth. When the preparation is prepared, additives commonly used in usual oral drugs as pharmaceutical ingredients, such as carrier, excipient, binder, disintegrating agent, lubricant, stabilizer, flavoring agent, diluent, surfactant and solvent, can be used.

Further, so long as the effect of the present invention is not degraded, the extract of *Citrus depressa* or the polymethoxyflavonoid may be used together with an agent or pharmaceutical composition having an IGF-1 production-promoting action or a protein synthesis-promoting action, which is already known or will be found in future, or an agent or pharmaceutical composition having a muscle atrophy inhibition action, which is already known or will be found in future. The pharmaceutical composition used together may be comprised in the agent of the present invention as one of active ingredients, or may not be comprised in the agent of the present invention, but combined as a separate drug with the agent of the present invention to form a commercial product.

Examples of the carrier and excipient used for the aforementioned preparation include lactose, glucose, sucrose, mannitol, potato starch, corn starch, calcium carbonate, calcium phosphate, calcium sulfate, crystalline cellulose, glycyrrhizae radix pulverata, gentianae radix pulverata, and so forth, and examples of the binder include, for example, starch, gelatin, syrup, polyvinyl alcohol, polyvinyl ether, polyvinylpyrrolidone, hydroxypropylcellulose, ethylcellulose, methylcellulose, carboxymethylcellulose, and so forth.

Examples of the disintegrating agent include starch, agar, gelatin powder, sodium carboxymethylcellulose, calcium carboxymethylcellulose, crystalline cellulose, calcium carbonate, sodium hydrogencarbonate, sodium arginate, and so forth.

Examples of the lubricant include magnesium stearate, hydrogenated vegetable oil, Macrogol, and so forth, and examples of the colorant include Red No. 2, Yellow No. 4, Blue No. 1, which are allowed to be added to drugs, and so forth.

Tablets and granules can be coated with sucrose, hydroxypropylcellulose, purified shellac, gelatin, sorbitol, glycerol, ethylcellulose, hydroxypropylcellulose, hydroxypropylmethylcellulose, polyvinylpyrrolidone, cellulose acetate phthalate, hydroxypropylmethylcellulose phthalate, methyl methacrylate, methacrylic acid polymer, and so forth, as required.

One aspect of the present invention is use of a polymethoxyflavonoid or an extract of *Citrus depressa* comprising a polymethoxyflavonoid in preparation of a drug for promoting IGF-1 production. Another aspect of the present invention is a polymethoxyflavonoid or an extract of *Citrus depressa* comprising a polymethoxyflavonoid to be used for promoting IGF-1 production. Still another aspect of the present invention is a method for promoting IGF-1 production comprising administering a polymethoxyflavonoid or an extract of *Citrus depressa* comprising a polymethoxyflavonoid to an animal. In these aspects, the extract of *Citrus depressa* is an extract of *Citrus depressa* comprising 0.3 mass % or more of the polymethoxyflavonoid.

Amount of the polymethoxyflavonoid or extract of *Citrus depressa* comprising a polymethoxyflavonoid comprised in the agent of the present invention is not particularly limited, and can be appropriately chosen. However, when an extract of *Citrus depressa* comprising a polymethoxyflavonoid is used, for example, the amount is preferably 0.01 mass % or more, more preferably 0.1 mass % or more, still more preferably 1 mass % or more, and particularly preferably 10 mass % or more, in terms of the amount of the solid matter comprised in the extract of *Citrus depressa*. Alternatively, the amount of the extract of *Citrus depressa* comprised in the agent of the present invention is preferably 0.1 mass % or more, more preferably 0.3 mass % or more, still more preferably 0.6 mass % or more, further preferably 1 mass % or more, still further preferably 3 mass % or more, and particularly preferably 10 mass % or more, as content of the polymethoxyflavonoid in terms of solid matter. Although the maximum content of the extract of *Citrus depressa* is not particularly limited, it may be, for example, 95 mass % or less, 90 mass % or less, or 50 mass % or less, in terms of the amount of the solid matter in the extract of *Citrus depressa*, or it may be, for example, 95 mass % or less, 80 mass % or less, 60 mass % or less, or 40 mass % or less, in terms of the amount of the polymethoxyflavonoid.

Further, when the polymethoxyflavonoid is used, amount of the polymethoxyflavonoid comprised in the agent is preferably 0.001 mass % or more, more preferably 0.01 mass % or more, still more preferably 0.1 mass % or more, further preferably 0.3 mass % or more, still further preferably 0.6 mass % or more, still more further preferably 1 mass % or more, still more further preferably 3 mass % or more, and particularly preferably 10 mass % or more, in terms of solid matter. Although the maximum content of the polymethoxyflavonoid is not particularly limited, it may be, for example, 95 mass % or less, 80 mass % or less, 60 mass % or less, 40 mass % or less, or 30 mass % or less.

When nobiletin is used as the polymethoxyflavonoid, the amount of nobiletin comprised in the agent is preferably 0.0007 mass % or more, more preferably 0.07 mass % or more, still more preferably 0.2 mass % or more, further preferably 0.4 mass % or more, still further preferably 2.0 mass % or more, and particularly preferably 5 mass % or more, in terms of solid matter. Although the maximum content of nobiletin is not particularly limited, it may be, for example, 95 mass % or less, 70 mass % or less, 50 mass % or less, 30 mass % or less, or 10 mass % or less.

When tangeretin is used as the polymethoxyflavonoid, the amount of tangeretin comprised in the agent is preferably 0.0004 mass % or more, more preferably 0.04 mass % or more, still more preferably 0.1 mass % or more, further preferably 0.2 mass % or more, still further preferably 1 mass % or more, and particularly preferably 2 mass % or more, in terms of solid matter. Although the maximum content of tangeretin is not particularly limited, it may be, for example, 95 mass % or less, 70 mass % or less, 50 mass % or less, 30 mass % or less, or 10 mass % or less.

When two or more kinds of polymethoxyflavonoids, such as nobiletin, tangeretin, and other polymethoxyflavonoids, are used, the contents thereof in the agent may be appropriately chosen to be within the aforementioned ranges. For example, when both nobiletin and tangeretin are used as the polymethoxyflavonoid, although it is sufficient that amount of at least one of them is within any of the aforementioned ranges, it is preferred that amounts of the both compounds are within any of the aforementioned ranges.

The agent of the present invention has an IGF-1 production-promoting action. It is known that IGF-1 is involved in a wide variety of diseases and actions including central nerve diseases (dementia such as Alzheimer's disease, etc.), cardiovascular diseases (myocardial infarction, cerebral infarction, hypertension, etc.), metabolic disorders (obesity, diabetes, hypercholesterolemia, etc.), digestive system and visceral disorders (ulcer, decreased liver function, etc.), locomotorium diseases (rheumatoid arthritis, arthritis, etc.), dermatologic disorders (skin aging, epilation, etc.), immunity activation actions (NK cell activation, etc.), and so forth (Japanese Patent Laid-open (Kokai) No. 2011-157345).

The agent of the present invention can be used for amelioration of growth hormone deficiency in adults, growth hormone deficiency dwarfism, central nerve diseases (dementia such as Alzheimer's disease, etc.) (Cell Mol. Neurobiol., 2010 April, 30(3):347-60; Brain Res., 2009 Dec. 15, 1303:179-94), cardiovascular diseases (myocardial infarction, cerebral infarction, hypertension, etc.) (Clin. Endocrinol. (Oxf), 2005, 63:470-476; Circulation, 2004, 110:2260-2265), metabolic disorders (obesity, diabetes, hypercholesterolemia, etc.) (Brain Res., 2009 Dec. 15, 1303: 179-94), digestive system and visceral disorders (ulcer, decreased liver function, etc.) (J. Surg. Res., 2008, 145:279-286), locomotorium diseases (rheumatoid arthritis, arthritis, sarcopenia, etc.) (Int. J. Biochem. Cell Biol., 2005 October, 37(10):1974-84), dermatologic disorders (skin aging, epilation, etc.) (Ann. Dermatol., 2012 February, 24(1):26-31), and so forth, as well as immunity activation (NK cell activation etc.), and so forth. For example, there can be contemplated use as applications for reduction of visceral fat, anti-senility, prevention and treatment of diseases, and so forth based on elevation of IGF-1 level.

Further, the agent of the present invention exhibits a protein synthesis-promoting action via the IGF-1 production-promoting action. In a preferred embodiment of the IGF-1 production-promoting agent of the present invention, it is used for promotion of protein synthesis. Therefore, in this specification, the "IGF-1 production-promoting action" and "IGF-1 production-promoting agent" can be read as "protein synthesis-promoting action" and "protein synthesis-promoting agent", respectively.

Because of the protein synthesis-promoting action of the agent of the present invention, there can be contemplated use thereof for improvement in sport performance, growth promotion, promotion of physical strengthening by body building etc., promotion of metabolism, strengthening of muscles, recovery from muscular atrophy, and so forth.

As for the IGF-1 production-promoting agent of the present invention, especially the IGF-1 production-promoting agent used for promotion of protein synthesis, it is preferred that use as a muscular atrophy inhibitor is excluded from use thereof. The muscular atrophy mentioned above refers to a state that muscle mass decreases due to decrease in number of muscle fibers and decrease in volume of muscle fibers.

Time for administration of the agent of the present invention is not particularly limited, and can be appropriately chosen according to a state of an object of the administration.

Dose of the agent of the present invention is appropriately chosen depending on age, sex, state of the object of administration, other conditions, and so forth. The dose is preferably chosen to be in the range of 0.01 to 500 (mg/kg/day), and more preferably 1 to 250 (mg/kg/day), as a standard in terms of the amount (mg) per body weight 1 kg per day of the solid matter comprised in the extract of *Citrus depressa*.

The agent can be administered at a dose of preferably 0.03 (mg/kg/day) or more, more preferably 0.3 (mg/kg/day) or more, still more preferably 3 (mg/kg/day) or more, and particularly preferably 30 (mg/kg/day) or more, as a standard in terms of the amount (mg) per body weight 1 kg per day of the polymethoxyflavonoid comprised in the solid matter of the extract of *Citrus depressa*. In this case, the maximum dose is preferably 150 (mg/kg/day) or less, more preferably 120 (mg/kg/day) or less, still more preferably 90 (mg/kg/day) or less, and particularly preferably 60 (mg/kg/day) or less.

The dose of the agent of the present invention in terms of the amount (mg) per body weight 1 kg per day of the polymethoxyflavonoid is preferably (0.03 mg/kg/day) or more, more preferably 0.3 (mg/kg/day) or more, still more preferably 3 (mg/kg/day) or more, and particularly preferably 30 (mg/kg/day) or more, as a standard. The maximum dose in this case is preferably 150 (mg/kg/day) or less, more preferably 120 (mg/kg/day) or less, still more preferably 90 (mg/kg/day) or less, and particularly preferably 60 (mg/kg/day) or less.

The dose in terms of the amount (mg) per body weight 1 kg per day of nobiletin is preferably 0.02 (mg/kg/day) or more, more preferably 0.2 (mg/kg/day) or more, still more preferably 2 (mg/kg/day) or more, and particularly preferably 20 (mg/kg/day) or more, as a standard. The maximum dose in this case is preferably 90 (mg/kg/day) or less, more preferably 72 (mg/kg/day) or less, still more preferably 54 (mg/kg/day) or less, and particularly preferably 36 (mg/kg/day) or less.

The dose in terms of the amount (mg) per body weight 1 kg per day of tangeretin is preferably 0.01 (mg/kg/day) or more, more preferably 0.1 (mg/kg/day) or more, still more preferably 1 (mg/kg/day) or more, and particularly preferably 10 (mg/kg/day) or more, as a standard. The maximum dose in this case is preferably 60 (mg/kg/day) or less, more preferably 48 (mg/kg/day) or less, still more preferably 36 (mg/kg/day) or less, and particularly preferably 24 (mg/kg/day) or less.

Further, when the administration period is long, for example, one to several months or longer, the effect can be expected even with a dose of the agent of about 1/10 to 1/100 of the aforementioned ranges.

Regardless of the administration period, the daily dose of the agent can be administered one time a day, or two or more times a day as divided portions.

The agent of the present invention, or the extract of *Citrus depressa* or polymethoxyflavonoid as the active ingredient of the agent may be added to diets (drink or food).

Further, it is also possible to add the polymethoxyflavonoid, the extract of *Citrus depressa* comprising a polymethoxyflavonoid, or the agent of the present invention to a drink or food as an active ingredient to produce a drink or food having an IGF-1 production-promoting action as one embodiment of the IGF-1 production-promoting agent.

Forms and properties of the food and drink are not particularly limited so long as the effect of the polymethoxyflavonoid or the extract of *Citrus depressa* is not degraded, and they can be orally ingested, and they can be prepared by using usual raw materials used for foods and drinks and usual methods, except that the polymethoxyflavonoid or the extract of *Citrus depressa* is added.

Forms of such foods as mentioned above are not particularly limited, and they may be in the form of liquid, paste, gelled solid, powder, or the like. Examples include, for example, tablet confectioneries, and liquid diets, as well as, for example, flour products such as bread, macaroni, spaghetti, noodles, cake mix, fry powder and bread crumbs; ready-to-eat foods such as instant noodles, pot noodles, retort and cooked foods, canned cooking, foods for microwave heating, instant soup and stew, instant miso soup and Japanese clear soup, canned soup, freeze-dried foods, and other ready-to-eat foods; processed agricultural products such as canned agricultural products, canned fruits, jams and marmalades, pickles, cooked beans, dry agricultural products, and cereals (processed grain products); processed marine products such as canned marine products, fish ham and sausages, seafood paste products, marine dainties, and tsukudani (marine products boiled in soy source); processed livestock products such as canned livestock products and pastes, and livestock meat ham and sausages; milks and dairy products such as processed milk, milk drinks, yoghurts, lactic acid drinks, cheese, ice creams, modified milk powders, creams, and other dairy products; oils and fats such as butter, margarines, and vegetable oils; basic seasoning such as soy sauce, miso, sauces, processed tomato seasoning, mirin, and vinegars; complex seasonings and foods such as cooking mix, curry powder or roux, sauces for dipping, dressings, noodle soups, spices, and other complex seasonings; frozen foods such as frozen food materials, semi-cooked frozen foods, and cooked frozen foods; confectioneries such as caramel candies, candies, chewing gums, chocolates, cookies, biscuits, cakes, pies, snacks, crackers, Japanese sweets, rice confectioneries, bean confectioneries, dessert pastries, jellies, and other confectioneries; beverages such as carbonated drinks, natural fruit juices, fruit juice drinks, fruit juice soft drinks, fruit pulp drinks, fruit drinks with fruit pulp, vegetable based drinks, soy milk, soy milk drinks, coffee drinks, tea drinks, powdered drinks, concentrated drinks, sports drinks, nutritional beverage, alcoholic drinks, and other beverages; other commercial foods such as baby foods, rice seasonings, and seaweed seasonings for boiled rice soaked with tea; modified milk powder for infants; enteral nutrients; functional foods (foods for specified health use, foods with nutrient function claims), and so forth.

Furthermore, by adding the polymethoxyflavonoid or extract of *Citrus depressa* comprising a polymethoxyflavonoid, or the agent of the present invention to a feed as an active ingredient, a feed having an IGF-1 production-promoting action can be prepared, as one embodiment of the IGF-1 production-promoting agent.

Form of the feed is not particularly limited. For example, the feed can be prepared by blending cereals such as corn, wheat, barley, rye and milo; vegetable oil meals such as soybean oil meal, rapeseed oil meal, coconut oil meal and linseed oil meal; brans such as wheat bran, rice bran, and defatted rice bran; manufactured meals such as corn gluten meal and corn jam meal; animal or fish-derived feeds such as fish meal, skim milk powder, whey, yellow grease and tallow; yeasts such as torula yeast and brewer's yeast; mineral material feeds such as tribasic calcium phosphate and calcium carbonate; oils and fats; monomeric amino acids; saccharides, and so forth. Examples of the form of the feed include, for example, pet food, livestock feed, fish breeding feed, and so forth.

The amount of the polymethoxyflavonoid or extract of *Citrus depressa* comprised in the food or drink (including feed) of the present invention is not particularly limited, and may be appropriately chosen. However, for example, when an extract of *Citrus depressa* comprising a polymethoxyflavonoid is used, the amount thereof is preferably 1 mass % or more in terms of the amount of solid matter comprised in the extract of *Citrus depressa*.

Alternatively, the amount of the extract of *Citrus depressa* comprised in the food or drink is preferably 0.3 mass % or more, more preferably 0.6 mass % or more, still more preferably 3 mass % or more, and particularly preferably 10 mass % or more, in terms of content of the polymethoxyflavonoid. Although the maximum content of the extract of *Citrus depressa* is not particularly limited, it may be, for example, 95 mass % or less, 50 mass % or less, 30 mass % or less, 20 mass % or less, or 10 mass % or less, in terms of the amount of solid matter in the extract of *Citrus depressa*, or it may be, for example, 95 mass % or less, 70 mass % or less, 60 mass % or less, 50 mass % or less, or 40 mass % or less, in terms of the amount of the polymethoxyflavonoid.

Further, when the polymethoxyflavonoid is used, the amount of the polymethoxyflavonoid comprised in the food or drink is preferably 0.3 mass % or more, more preferably 0.6 mass % or more, still more preferably 3.0 mass % or more, and particularly preferably 10 mass % or more, in terms of solid matter. Although the maximum content of the polymethoxyflavonoid is not particularly limited, it may be, for example, 95 mass % or less, 70 mass % or less, 60 mass % or less, 50 mass % or less, or 40 mass % or less.

When nobiletin is used, the amount of nobiletin comprised in the food or drink is preferably 0.2 mass % or more, more preferably 0.4 mass % or more, still more preferably 2.0 mass % or more, and particularly preferably 5 mass % or more, in terms of solid matter. Although the maximum content of nobiletin is not particularly limited, it may be, for example, 95 mass % or less, 70 mass % or less, 50 mass % or less, 30 mass % or less, or 10 mass % or less.

When tangeretin is used, the amount of tangeretin comprised in the food or drink is preferably 0.1 mass % or more, more preferably 0.2 mass % or more, still more preferably 1.0 mass % or more, and particularly preferably 2 mass % or more, in terms of solid matter. Although the maximum content of tangeretin is not particularly limited, it may be, for example, 95 mass % or less, 70 mass % or less, 50 mass % or less, 30 mass % or less, or 10 mass % or less.

If such ingredients as milk protein (casein), whey protein (whey), soy protein, whey peptides, branched-chain amino acids (valine, leucine, isoleucine), HMB, glutamine, arginine, ornithine, citrulline, creatine, carnitine, nucleic acids (DNA, RNA), vitamin B6, vitamin C, vitamin D, vitamin E, zinc, magnesium, various polymethoxyflavonoids, and various polyphenols are ingested together with the food or drink of the present invention, it can be expected that higher IGF-1 production-promoting effect is obtainable. These ingredients may be added to the food or drink of the present invention.

Further, the food or drink (including feed) of the present invention desirably comprises 5 mg or more, preferably 18 mg or more, and more preferably 180 mg or more, of the extract of *Citrus depressa* in terms of solid matter in an amount thereof for single ingestion.

Further, the food or drink (including feed) of the present invention desirably comprises 1.8 mg or more, preferably 18 mg or more, and more preferably 180 mg or more, of the polymethoxyflavonoid in terms of solid matter in an amount thereof for single ingestion.

Further, the food or drink (including feed) of the present invention desirably comprises 1.2 mg or more, preferably 12 mg or more, and more preferably 120 mg or more, of nobiletin in terms of solid matter in an amount thereof for single ingestion.

Further, the food or drink (including feed) of the present invention desirably comprises 0.6 mg or more, preferably 6 mg or more, and more preferably 60 mg or more, of tangeretin in terms of solid matter in an amount thereof for single ingestion.

EXAMPLES

Hereafter, the present invention will be more specifically explained with reference to examples. However, the present invention is not limited to these examples.

Example 1

The IGF-1 production-promoting effect of extract of *Citrus depressa* was evaluated in mice under exercise load conditions.

The extract of *Citrus depressa* used (commercial product, ARKRAY) was one obtained by adding cyclodextrin as a clathrating agent to an extract from squeezed residue of *Citrus depressa* fruits extracted with water-comprising ethanol, and had the following composition according to the usual specification thereof.

| | |
|---|---|
| Solid matter | 92 mass % or more |
| Cyclodextrin | 50 mass % |
| Polymethoxyflavonoids | 10 mass % or more |

Nobiletin content and tangeretin content of the extract of *Citrus depressa* (comprising cyclodextrin) used for the following experiment were 6.9 mass % and 3.4 mass %, respectively.

Male C57BL/6J mice (10-week old) were preliminarily bred for one week, and divided into three groups (control group (Cont), exercise group (Run), and exercise+*Citrus depressa* extract administration group (Run+SE), n=8 for the Cont and Run+SE groups, and n=7 for the Run group).

For the mice of the Run and Run+SE groups, a treadmill exercise acclimation period of two weeks (frequency, three days/week; exercise load was gradually increased (gradient, 5 to 20%; speed, 5 to 20 m/minute; time, 30 to 60 minutes/day)) was set, and then the mice were subjected to exercise load for 10 weeks (gradient, 20%; 20 m/minute; 60 minutes/day; 5 days/week).

At the same time, the mice of the Cont and Run groups were fed with standard feed AIN-93M (CLEA Japan), and the mice of the Run+SE group were fed with AIN-93M comprising the extract of *Citrus depressa* at a ratio of 1 mass % over 12 weeks including the exercise acclimation period (free oral ingestion).

Twelve weeks after the change of the feed, the mice were dissected, and the livers and serum were collected. The expression of IGF-1 mRNA in the liver and concentration of IGF-1 in the serum were measured by real-time PCR and ELISA, respectively.

The collected liver tissue was immersed in RNA later (solution for stabilizing RNA in tissues, Ambion), left standing overnight at 4° C., and then stored at −20° C. mRNA was extracted from the liver tissue by using RNeasy Kit (QIAGEN), and reverse-transcribed by using Thermal Cycler Veriti (Applied Biosystems) and High Capacity cDNA Reverse Transcription Kit (Applied Biosystems) to obtain cDNA. The IGF-1 mRNA expression was measured by real-time PCR performed by using the cDNA obtained above, the primers for amplifying IGF-1 cDNA (Assay ID Mm004395960_ml, Applied Biosystems), real-time PCR apparatus (7500 Fast Real-Time PCR System, Applied Biosystems), and TaqMan Gene Expression Assay (Applied Biosystems).

The measurement was performed according to the protocols attached to the kits and the general conditions set in the apparatuses. The amount of gene expression was quantified and analyzed as relative amount based on that obtained in the Cont group, which was taken as 1. Statistically significant differences were examined by statistical processings based on the Tukey test or Tukey-Kramer test.

The serum IGF-1 concentration was measured by using IGF-1 ELISA Kit (RSD) according to the protocol attached to the kit.

The results representing variation of the expression of the liver IGF-1 mRNA (AU) provided by the administration of the extract of *Citrus depressa* in the mice under the exercise load are shown in Table 1, and the results representing variation of the serum IGF-1 concentration provided by the administration of the extract of *Citrus depressa* in the mice under the exercise load are shown in Table 2.

In Tables 1 and 2, Cont represents the control group, Run represents the exercise group, and Run+SE represents the exercise+*Citrus depressa* extract administration group.

The IGF-1 mRNA expression in the liver was 1.00±0.27 for the Cont group, but it was 1.23±0.30 for the Run group, and 1.67±0.17 for the Run+SE group. Thus, the amount increased to 135.7% in the Run+SE group compared with the Run group (p<0.05, S.D. represents standard deviation). On the basis of this result, it was confirmed that expression of IGF-1 mRNA is promoted in the liver by ingestion of the extract of *Citrus depressa* comprising polymethoxyflavonoids.

TABLE 1

| Group | Expression of IGF-1 mRNA in liver (AU) | S.D. | |
|---|---|---|---|
| Cont | 1.00 | 0.27 | *1 |
| Run | 1.23 | 0.30 | *1 |
| Run + SE | 1.67 | 0.17 | *1 *1 |

*1: p < 0.05

Further, the IGF-1 concentration in the serum was 101±56 ng/mL for the Cont group, but it was 97±38 ng/mL for the Run group and 179±40 ng/mL for the Run+SE group. Thus, the IGF-1 concentration increased to 184% in the Run+SE group compared with the Run group (p=0.09, S.E. represents standard error).

As described above, it was confirmed that the systemic IGF-1 production is promoted by ingestion of the extract of *Citrus depressa* comprising polymethoxyflavonoids.

TABLE 2

| Group | Serum IGF-1 concentration (ng/mL) | S.E. | |
|---|---|---|---|
| Cont | 101 | 56 | |
| Run | 97 | 38 | †1 |
| Run + SE | 179 | 40 | †1 |

†1: p = 0.09

Example 2

The protein synthesis-promoting effects of ingestions of the extract of *Citrus depressa*, polymethoxyflavonoid, nobiletin and tangeretin on recovery from muscular atrophy were evaluated in mice in which muscular atrophy was induced by tail suspension over two weeks.

The extract of *Citrus depressa* used for the following experiment was the same as that used in Example 1. As the polymethoxyflavonoid, a mixture of 67 mass % of nobiletin and 33 mass % of tangeretin was used.

Male C57BL/6J mice (10-week old) were preliminarily bred for one week, and divided into six groups (control group (Cont), standard feed administration after tail suspension group (Fix), *Citrus depressa* extract administration after tail suspension group (Fix+SE), polymethoxyflavonoid administration after tail suspension group (Fix+PMF), nobiletin administration after tail suspension group (Fix+NOB), and tangeretin administration after tail suspension group (Fix+TAN), n=8 for the Cont, Fix, Fix+SE, Fix+PMF, Fix+NOB, and Fix+TAN groups).

After the preliminary breeding, muscular atrophy was induced in the mice of the Fix and Fix+SE groups by tail suspension for two weeks. During this period, free oral ingestion of the standard feed AIN-93M (CLEA Japan) was allowed for the mice of the three groups.

After the tail suspension period, AIN-93M was fed to the mice of the Cont and Fix groups, AIN-93M comprising 1 mass % of the extract of *Citrus depressa* was fed to the mice of the Fix+SE group, AIN-93M comprising 0.1 mass % of the polymethoxyflavonoid (mixture of 67 mass % of nobiletin and 33 mass % of tangeretin, nobiletin and tangeretin were produced by Tokyo Chemical Industry) was fed to the mice of the Fix+PMF group, AIN-93M comprising 0.07 mass % of nobiletin (Tokyo Chemical Industry) was fed to the mice of the Fix+NOB group, and AIN-93M comprising 0.04 mass % of tangeretin (Tokyo Chemical Industry) was fed to the mice of the Fix+TAN group, each for 3 days (free oral ingestion).

On day 4 after the change of the feed, the mice were dissected, and the serum IGF-1 concentration, expression of follistatin mRNA in the gastrocnemius, expression of IGF-1 mRNA in the gastrocnemius, and phosphorylation ratio (β+γ) of p70S6K1 in the gastrocnemius were evaluated.

It is known that follistatin binds to the TGF-β family members (TGF-β, activin, myostatin, etc.) to control or suppress the activities of them. In particular, there have been reported cytostatic action for TGF-β, growth hormone secretion suppression action for activin, and action on differentiation of stem cell into fat cell for myostatin, and it is considered that, when follistatin inhibits these actions, protein synthesis is promoted. Therefore, expression of follistatin mRNA serves as a marker of protein synthesis.

Further, phosphorylation ratio of p70S6K1 also serves as a marker of protein synthesis.

The serum IGF-1 concentration was measured in the same manner as that used in Example 1. The expression of follistatin mRNA in the gastrocnemius was measured in the same manner as that used in Example 1, except that the hind leg gastrocnemius was extracted from each rat, and Assay ID Mm00514982_m1 (Applied Biosystems) was used as the primer. Phosphorylation of p70S6K1 was measured by the chemiluminescence method using ECL Western Blotting Analysis System (GE Healthcare Life Science) for bands obtained in SDS-PAGE, then transferred to a PVDF membrane, and bound with primary antibodies (p70S6 kinase α (C-18), SantaCruz Biotechnology) and secondary antibodies (ECL Anti-Rabbit IgG).

The results of the measurements are shown in Tables 3 to 6.

The results shown in Table 3 show variation of the serum IGF-1 concentration provided by the administration of the extract of *Citrus depressa* at the time of recovery from muscular atrophy in mice in which the muscular atrophy was induced by tail suspension. In the table, Cont represents the control group, Fix represents the standard feed administration at the time of recovery from muscular atrophy after tail suspension group, and Fix+SE represents the *Citrus depressa* extract administration at the time of recovery from muscular atrophy after tail suspension group.

The results shown in Table 4 show variation of the expression of follistatin mRNA provided by the administration of the polymethoxyflavonoid at the time of recovery from muscular atrophy in mice in which the muscular atrophy was induced by tail suspension. Cont represents the control group, Fix represents the standard feed administration at the time of recovery from muscular atrophy after tail suspension group, and Fix+PMF represents the polymethoxyflavonoid administration at the time of recovery from muscular atrophy after tail suspension group.

The results shown in Table 5 show variation of the expression of IGF-1 mRNA in the gastrocnemius provided by the administration of nobiletin at the time of recovery from muscular atrophy in mice in which the muscular atrophy was induced by tail suspension. Cont represents the control group, Fix represents the standard feed administration at the time of recovery from muscular atrophy after tail suspension group, and Fix+NOB represents the nobiletin administration at the time of recovery from muscular atrophy after tail suspension group.

The results shown in Table 6 show variation of the phosphorylation ratio of p70S6K1 in the gastrocnemius provided by the administration of tangeretin at the time of recovery from muscular atrophy in mice in which the muscular atrophy was induced by tail suspension. Cont represents the control group, Fix represents the standard feed administration at the time of recovery from muscular atrophy after tail suspension group, and Fix+TAN represents the tangeretin administration at the time of recovery from muscular atrophy after tail suspension group.

The serum IGF-1 concentration was 252±78 ng/mL for the Cont group, but it was 294±42 ng/mL for the Fix group and 325±34 ng/mL for the Fix+SE group, and thus it increased to 110.5% in the Fix+SE group compared with the Fix group (Table 3). On the basis of this result, it was confirmed that although increase of the IGF-1 concentration was seen at the time of recovery from the atrophy compared with the usual time, the IGF-1 concentration was further increased by the ingestion of the extract of *Citrus depressa*. Since the ingestion was allowed only for 3 days in this experiment, significant difference was not seen between the Fix group and the Fix+SE group. However, it is considered that prolonged ingestion of the extract of *Citrus depressa* can provide IGF-1 production-promoting action and protein synthesis-promoting action.

TABLE 3

| Group | Serum IGF-1 concentration (ng/mL) | S.D. | |
|---|---|---|---|
| Cont | 252 | 78 | *2 |
| Fix | 294 | 42 | |
| Fix + SE | 325 | 34 | *2 |

*2: p < 0.05

The measurement result of the expression of follistatin mRNA was 1.00±0.27 for the Cont group, but it was 1.10±0.20 for the Fix group and 1.30±0.21 for the Fix+PMF group, and thus the expression of follistatin mRNA increased to 118% in the Fix+PMF group compared with the Fix group (Table 4). On the basis of this result, it was confirmed that although increase of the expression of follistatin mRNA was seen at the time of recovery from the atrophy compared with the usual time, the expression of follistatin mRNA was further increased by the ingestion of the polymethoxyflavonoid. Since the ingestion was allowed only for 3 days in this experiment, significant difference was not seen between the Fix group and the Fix+PMF group. However, it is considered that prolonged ingestion of the polymethoxyflavonoid can provide follistatin mRNA expression-promoting action and protein synthesis-promoting action.

TABLE 4

| Group | Expression of follistatin mRNA (AU) | S.D. | | |
|---|---|---|---|---|
| Cont | 1.00 | 0.27 | *3 | |
| Fix | 1.10 | 0.20 | | †2 |
| Fix + PMF | 1.30 | 0.21 | *3 | †2 |

*3: p < 0.05
†2: p = 0.07

The measurement result of the expression of IGF-1 mRNA in the gastrocnemius was 1.00±0.13 for the Cont group, but the expression of IGF-1 mRNA was 1.64±0.15 for the Fix group and 1.75±0.40 for the Fix+NOB group (Table 5), and thus the expression of IGF-1 mRNA increased to 107% in the Fix+NOB group compared with the Fix group. On the basis of this result, it was confirmed that although increase of the expression of IGF-1 mRNA was seen at the time of recovery from the atrophy compared with the usual time, the expression of IGF-1 mRNA was further increased by the ingestion of nobiletin. Since the ingestion was allowed only for 3 days in this experiment, significant difference was not seen between the Fix group and the Fix+NOB group. However, it is considered that prolonged ingestion of nobiletin can provide IGF-1 production-promoting action and protein synthesis-promoting action.

TABLE 5

| Group | Expression of IGF-1 mRNA in gastrocnemius (AU) | S.D. | | |
|---|---|---|---|---|
| Cont | 1.00 | 0.13 | *4 | *5 |
| Fix | 1.64 | 0.15 | *4 | |
| Fix + NOB | 1.75 | 0.40 | | *5 |

*4: $p < 0.01$
*5: $p < 0.01$

The measurement result of the phosphorylation ratio of p70S6K1 in the gastrocnemius was 26.4±4.8 for the Cont group, but it was 42.8±10.2 for the Fix group and 47.8±11.8 for the Fix+TAN group (Table 6), and thus the phosphorylation ratio of p70S6K1 increased to 112% in the Fix+TAN group compared with the Fix group. On the basis of this result, it was confirmed that although increase of the phosphorylation ratio of p70S6K1 was also seen at the time of recovery from the atrophy compared with the usual time, the phosphorylation ratio of p70S6K1 was further increased by the ingestion of tangeretin. Since the ingestion was allowed only for 3 days in this experiment, significant difference was not seen. However, it is considered that prolonged ingestion of tangeretin can provide protein synthesis-promoting action.

TABLE 6

| Group | Phosphorylation ratio of p70S6K1 in gastrocnemius (β + γ) (%) | S.D. | | |
|---|---|---|---|---|
| Cont | 26.4 | 4.8 | *6 | *7 |
| Fix | 42.8 | 10.2 | *6 | |
| Fix + TAN | 47.8 | 11.8 | | *7 |

*6: $p < 0.01$
*7: $p < 0.01$

Example 3

The protein synthesis promotion effect of ingestion of the extract of *Citrus depressa* was evaluated in mice in which muscular atrophy was induced by plaster fixation over two weeks.

The extract of *Citrus depressa* used for the following experiment was the same as that used in Example 1.

Male SD rats (18-month old) were preliminarily bred for one week, and divided into three groups (control group (Cont), hind leg fixation+standard feed administration group (Fix), and hind leg fixation+*Citrus depressa* extract administration group (Fix+SE), n=7 for the Cont and Fix groups, n=6 for the Fix+SE group).

The standard feed AIN-93M (CLEA Japan) was given to the rats of the Cont and Fix groups, and AIN-93M comprising 1 mass % of the extract of *Citrus depressa* was given to the rats of the Fix+SE group for 14 days (free oral ingestion).

After feeding over 14 days, ingestion of each feed was continuously allowed, and plaster fixation was performed for the rats of the Fix and Fix+SE groups for seven days to induce muscular atrophy.

On day 8 after the start of the plaster fixation, rats were dissected, the gastrocnemius of right hind leg was extracted, and phosphorylation ratio of p70S6K1 was measured in the same manner as that used in Example 2.

The results showing variation of the phosphorylation ratio of p70S6K1 provided by the *Citrus depressa* extract administration in the rats in which muscular atrophy was induced by hind leg fixation are shown in Table 7. In table 7, Cont represents the control group, Fix represents the hind leg fixation+standard feed administration group, and Fix+SE represents the hind leg fixation+*Citrus depressa* extract administration group.

The phosphorylation ratio of p70S6K1 in the gastrocnemius was 26.3±1.9% for the Cont group, but it was 23.3±0.8% for the Fix group and 29.0±2.5% for the Fix+SE group, and thus it increased to 124.4% in the Fix+SE group compared with the Fix group ($p<0.05$). Thus, it was confirmed that the extract of *Citrus depressa* has a protein synthesis-promoting action also on the basis of the phosphorylation ratio of p70S6K1.

TABLE 7

| Group | Phosphorylation ratio of p70S6K1 in gastrocnemius (β + γ) (%) | S.D. | |
|---|---|---|---|
| Cont | 26.3 | 1.9 | |
| Fix | 23.3 | 0.8 | *8 |
| Fix + SE | 29.0 | 2.5 | *8 |

*8: $p < 0.05$

Example 4: Jelly Food

All of the following raw materials were dissolved in water, the solution was stirred, and then cyclodextrin-clathrated nobiletin was dissolved in the solution. The solution was sterilized in a conventional manner, and filled to prepare jelly food (100 g per piece) having the following composition. The content of nobiletin in one piece of the obtained jelly food was 70 mg. There were obtained results suggesting that long-term ingestion of two pieces per day of this food provides protein synthesis-promoting action based on IGF-1 production-promoting action.

| | |
|---|---|
| Dextrin (Matsutani Chemical Industry) | 25.0 mass % |
| Whey protein (Morinaga Milk Industry) | 12.5 mass % |
| Gelling agent (San-Ei Gen F.F.I.) | 0.3 mass % |
| Citric acid (San-Ei Gen F.F.I.) | 0.2 mass % |
| Sodium Ascorbate (DSM Nutrition) | 0.1 mass % |
| Nobiletin (Tokyo Chemical Industry) | 0.07 mass % |
| Cyclodextrin (San-Ei Gen F.F.I.) | 0.07 mass % |
| Flavor (San-Ei Gen F.F.I.) | 0.02 mass % |
| Vitamin D (San-Ei Gen F.F.I.) | $5.0 \times 10^{-7}$ mass % |
| Water | 61.74 mass % |

Example 5: Drink

All of the following raw materials were dissolved in water, the solution was stirred, and then cyclodextrin-clathrated tangeretin was dissolved in the solution. The solution was sterilized in a conventional manner, and filled to prepare drink (350 ml per bottle) having the following composition. The content of tangeretin in one bottle of the obtained drink was 28 mg. There were obtained results suggesting that long-term ingestion of two bottles per day of this drink provides protein synthesis-promoting action based on IGF-1 production-promoting action.

| | |
|---|---|
| Dextrin (Matsutani Chemical Industry) | 7.0 mass % |
| Protein hydrolysate (Morinaga Milk Industry) | 0.5 mass % |
| Citric acid (San-Ei Gen F.F.I.) | 0.2 mass % |
| Sodium Ascorbate (DSM Nutrition) | 0.2 mass % |
| Flavor (San-Ei Gen F.F.I.) | 0.02 mass % |
| Sweetener (San-Ei Gen F.F.I.) | 0.01 mass % |
| Tangeretin (Tokyo Chemical Industry) | 0.008 mass % |
| Cyclodextrin (San-Ei Gen F.F.I.) | 0.008 mass % |
| Water | 92.054 mass % |

Example 6: Tablet Confectionary

A mixture having the following composition was tableted in a conventional manner to produce tablet confectionaries having a weight of 250 mg per tablet. Content of the extract of *Citrus depressa* in 1 g of the obtained tablet confectionaries was 60 mg. Since the polymethoxyflavonoid content in the extract of *Citrus depressa* used as the raw material was 10% or higher, content of the polymethoxyflavonoid in 1 g of the tablet confectionaries was about 6 mg. There were obtained results suggesting that long-term ingestion of 16 tablets per day of this food provides protein synthesis-promoting action based on IGF-1 production-promoting action.

| | |
|---|---|
| Powder candy (Showa Sangyo) | 86.0 mass % |
| Extract of *Citrus depressa* (Arkray) | 6.0 mass % |
| Citric acid (San-Ei Gen F.F.I.) | 4.0 mass % |
| Flavor (San-Ei Gen F.F.I.) | 2.0 mass % |
| Emulsifier (Kao) | 2.0 mass % |

Example 7: Chewable Tablet

Chewable tablets having the following composition and a weight of 250 mg per tablet were produced in a conventional manner. Content of the extract of *Citrus depressa* in 1 g of the obtained chewable tablets was 200 mg. Since the polymethoxyflavonoid content in the extract of *Citrus depressa* used as the raw material was 10% or higher, content of the polymethoxyflavonoid in 1 g of the chewable tablets was about 20 mg. There were obtained results suggesting that long-term ingestion of 4 tablets per day of this food provides protein synthesis-promoting action based on IGF-1 production-promoting action.

| | |
|---|---|
| Erythritol (Mitsubishi Chemical Foods) | 68.0 mass % |
| Extract of *Citrus depressa* (Arkray) | 20.0 mass % |
| Citric acid (San-Ei Gen F.F.I.) | 7.0 mass % |
| Talc (San-Ei Gen F.F.I.) | 3.0 mass % |
| Flavor (San-Ei Gen F.F.I.) | 2.0 mass % |

Example 8: Enteral Nutrient (Concentrate Liquid Diet)

Casein and hardly digestible dextrin were dissolved in warm water, then dextrin, mineral mixture, vitamin mixture, and nobiletin clathrated with cyclodextrin were mixed with the solution, an emulsifier and soybean oil were added to the mixture, and the mixture was homogenized. The mixture was sterilized and filled in a conventional manner to prepare an enteral nutrient having the following composition. The mineral mixture and vitamin mixture mentioned below were obtained by mixing the ingredients in the amounts shown in Table 8. Content of nobiletin in 1000 ml of the obtained enteral nutrient was 46 mg. There were obtained results suggesting that long-term ingestion of 1000 ml per day of this diet provides protein synthesis-promoting action based on IGF-1 production-promoting action.

| | |
|---|---|
| Dextrin (Matsutani Chemical Industry) | 15.0 mass % |
| Casein sodium (Morinaga Milk Industry) | 4.0 mass % |
| Soybean oil (Taiyo Yushi) | 3.0 mass % |
| Hardly digestible dextrin (Matsutani Chemical Industry) | 1.0 mass % |
| Mineral mixture | 0.3 mass % |
| Emulsifier (San-Ei Gen F.F.I.) | 0.05 mass % |
| Vitamin mixture | 0.02 mass % |
| Flavor (San-Ei Gen F.F.I.) | 0.01 mass % |
| Nobiletin (Tokyo Chemical Industry) | 0.0046 mass % |
| Cyclodextrin (San-Ei Gen F.F.I.) | 0.0046 mass % |
| Water | 76.6108 mass % |

TABLE 8

(/1000 ml)

| Mineral mixture | |
|---|---|
| Na | 900 mg |
| K | 1500 mg |
| Ca | 750 mg |
| Mg | 380 mg |
| Fe | 11 mg |
| Vitamin mixture | |
| β-Carotene | 1800 μg |
| Vitamin D | 5 μg |
| α-Tocopherol | 12 mg |
| Vitamin B1 | 1.6 mg |
| Vitamin B2 | 1.8 mg |
| Vitamin B6 | 3 mg |
| Vitamin B12 | 3 μg |
| Vitamin C | 100 mg |

Example 9: Baked Confectionery

Baked confectionery having the following composition was produced in a conventional manner. Content of polymethoxyflavonoids in the obtained confectionery for one person (50 g) was 55 mg. It was observed that ingestion of this food resulted in providing protein synthesis-promoting effect. There were obtained results suggesting that long-term ingestion of this food in the amount for one person per day provides protein synthesis-promoting action based on IGF-1 production-promoting action.

| | |
|---|---|
| Granulated sugar (Nissin Sugar Manufacturing) | 30.0 mass % |
| Wheat flour (San-Ei Gen F.F.I., Inc.) | 30.0 mass % |
| Butter (Morinaga Milk Industry) | 15.0 mass % |
| Whole egg sauce (TAIYO KAGAKU) | 10.0 mass % |
| Whey peptide (Morinaga Milk Industry) | 9.0 mass % |
| Casein sodium (Tatua Japan) | 4.5 mass % |
| Extract of *Citrus depressa* (Arkray) | 1.1 mass % |
| Vitamin mixture (Riken Vitamin) | 0.2 mass % |
| Zinc gluconate (Oriental Yeast) | 0.1 mass % |
| Cupric gluconate (Oriental Yeast) | 0.09 mass % |
| Flavor (Nagaoka Perfumery) | 0.01 mass % |
| Vitamin D (Riken Vitamin) | $5.0 \times 10^{-6}$ mass % |

INDUSTRIAL APPLICABILITY

According to the present invention, an IGF-1 production-promoting agent is provided. The IGF-1 production-promoting agent of the present invention can be used as a drug. Further, since the IGF-1 production-promoting agent of the present invention uses the ingredients comprised in *Citrus depressa* as the active ingredient, it is highly safe, and can be used for food, drink, and so forth.

What is claimed is:

1. A method for treating a disease by promoting insulin-like growth factor-1 (IGF-1) production in a mammal comprising administering an IGF-1 production-promoting agent to the mammal wherein the agent comprises a polymethoxyflavonoid as an active ingredient, wherein the disease is sarcopenia.

2. The method according to claim 1, wherein the polymethoxyflavonoid is nobiletin and/or tangeretin.

3. The method according to claim 1, wherein the polymethoxyflavonoid is contained in an extract of *Citrus depressa* in an amount of 0.3 mass % or more in terms of solid matter as an active ingredient.

4. The method according to claim 3, wherein the agent further comprises a clathrating agent to make the polymethoxyflavonoid water-soluble.

5. The method according to claim 4, wherein the clathrating agent is cyclodextrin, and wherein content thereof is 0.1 to 95 mass % based on the total mass of the solid matter of the extract of *Citrus depressa* and cyclodextrin.

6. The method according to claim 3, wherein the extract of *Citrus depressa* comprises 0.2 mass % or more of nobiletin, and/or 0.1 mass % or more of tangeretin in terms of solid matter as an active ingredient.

7. The method according to claim 1, resulting in promotion of protein synthesis.

* * * * *